(12) United States Patent
Colman et al.

(10) Patent No.: US 6,384,297 B1
(45) Date of Patent: May 7, 2002

(54) WATER DISPERSIBLE PANTILINER

(75) Inventors: Charles Wilson Colman, Marietta, GA (US); Frank Steven Glaug, Chester Springs, PA (US); Yung Hsiang Huang, Appleton, WI (US); David Martin Jackson, Roswell, GA (US); John Edward Kerins, Neenah, WI (US); Jennifer Cappel Larson, Oshkosh, WI (US); Mary Jo Meyer, Neenah, WI (US); Pavneet Singh Mumick; Brian Keith Nortman, both of Appleton, WI (US); William Seal Pomplun, Neenah, WI (US); Fu-Jya Tsai; Susan Marie Weyenberg, both of Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/285,595

(22) Filed: Apr. 3, 1999

(51) Int. Cl.[7] .................................................. A61F 13/15
(52) U.S. Cl. ...................... 604/364; 604/365; 604/367; 604/386; 604/387; 604/389; 604/385.05
(58) Field of Search ................................. 604/359, 364, 604/365, 367, 375, 386, 387, 389, 385.05, 385.23

(56) References Cited

U.S. PATENT DOCUMENTS

| 3,338,992 A | 8/1967 | Kinney | 264/24 |
| 3,341,394 A | 9/1967 | Kinney | 161/72 |
| 3,375,448 A | 3/1968 | Newman et al. | 328/42 |
| 3,407,814 A | 10/1968 | George et al. | 128/290 |
| 3,480,016 A | 11/1969 | Costanza et al. | 128/284 |
| 3,502,763 A | 3/1970 | Hartmann | 264/210 |
| 3,521,638 A | 7/1970 | Parrish | 128/284 |

(List continued on next page.)

FOREIGN PATENT DOCUMENTS

| DE | 25 13 251 | 9/1976 | D01F/8/08 |
| GB | 2 295 553 | 6/1996 | A61F/13/15 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

"A Simple Test for Dispersion of Wet Chop Fiberglass in Water", published in the 1996 TAPPI Proceedings Nonwovens Conference.

Primary Examiner—John G. Weiss
Assistant Examiner—Michael Bogart
(74) Attorney, Agent, or Firm—James B. Robinson

(57) ABSTRACT

Disclosed herein is a water dispersible pantiliner which has a triggerably dispersible body side facing liner, a garment side facing baffle, and, optionally, a triggerably dispersible absorbent core disposed between the liner and baffle. The garment baffle may be biodegradable. In one embodiment, the invention has a peel strip overlaying a garment attachment adhesive layer which adhesively attaches the peel strip to the clothing of a wearer on one side and to one side of a baffle on the other. The baffle is in turn attached on a second side to a body facing side with a construction adhesive. The body facing side may be made from multiple layers such as a body side liner and absorbent layer.

1 Claim, 1 Drawing Sheet

U.S. PATENT DOCUMENTS

| | | | |
|---|---|---|---|
| 3,542,028 A | 11/1970 | Beebe | 128/290 |
| 3,542,615 A | 11/1970 | Dobo et al. | 156/181 |
| 3,550,592 A | 12/1970 | Bernardin | 128/290 |
| 3,554,788 A | 1/1971 | Fechillas | 117/140 |
| 3,556,919 A | 1/1971 | Johns et al. | 161/70 |
| 3,559,650 A | 2/1971 | Larson | 128/290 |
| 3,561,447 A | 2/1971 | Alexander | 128/290 |
| 3,563,241 A | 2/1971 | Evans et al. | 128/284 |
| 3,575,173 A | 4/1971 | Loyer | 128/290 |
| 3,580,253 A | 5/1971 | Bernardin | 128/290 |
| 3,581,744 A | 6/1971 | Voss et al. | 128/263 |
| 3,610,245 A | 10/1971 | Bernardin | 128/290 |
| 3,616,797 A | 11/1971 | Champaigne, Jr. et al. | 128/290 |
| 3,621,847 A | 11/1971 | Roberson | 128/290 |
| 3,635,221 A | 1/1972 | Champaigne, Jr. | 128/290 |
| 3,654,064 A | 4/1972 | Laumann | 161/156 |
| 3,654,928 A | 4/1972 | Duchane | 128/290 |
| 3,665,923 A | 5/1972 | Champaigne, Jr. | 128/290 |
| 3,683,919 A | 8/1972 | Ells | 128/290 |
| 3,692,618 A | 9/1972 | Dorschner et al. | 161/72 |
| 3,702,610 A | 11/1972 | Sheppard et al. | 128/284 |
| 3,707,430 A | 12/1972 | Costanza et al. | 161/123 |
| 3,724,462 A | 4/1973 | Hanke | 128/263 |
| 3,764,438 A | 10/1973 | Voss et al. | 156/425 |
| 3,800,797 A | 4/1974 | Tunc | 128/290 |
| 3,802,817 A | 4/1974 | Matsuki et al. | 425/66 |
| 3,804,092 A | 4/1974 | Tunc | 128/284 |
| 3,838,695 A | 10/1974 | Comerford et al. | 128/290 |
| 3,849,241 A | 11/1974 | Butin et al. | 161/169 |
| 3,881,487 A | 5/1975 | Schrading | 128/284 |
| 3,882,869 A | 5/1975 | Hanke | 128/263 |
| 3,891,584 A | 6/1975 | Ray-Chaudhuri et al. | 260/27 |
| 3,897,782 A | 8/1975 | Tunc | 128/290 |
| 3,911,917 A | 10/1975 | Hanke | 128/263 |
| 3,913,579 A | 10/1975 | Srinivasan et al. | 128/290 |
| 3,923,592 A | 12/1975 | George et al. | 162/168 |
| 3,939,836 A | 2/1976 | Tunc | 128/284 |
| 3,950,578 A | 4/1976 | Laumann | 427/378 |
| 3,952,347 A | 4/1976 | Comerford et al. | 5/335 |
| 3,952,745 A | 4/1976 | Duncan | 128/287 |
| 3,954,104 A | 5/1976 | Kraskin et al. | 128/263 |
| 4,002,171 A | * 1/1977 | Taft | 128/284 |
| 4,005,251 A | 1/1977 | Tunc | 536/59 |
| 4,011,871 A | 3/1977 | Taft | 128/284 |
| 4,099,976 A | 7/1978 | Kraskin et al. | 106/15 |
| 4,100,324 A | 7/1978 | Anderson et al. | 428/288 |
| 4,136,798 A | 1/1979 | Oberstein | 220/408 |
| 4,333,464 A | 6/1982 | Nakano | 128/290 |
| 4,340,563 A | 7/1982 | Appel et al. | 264/518 |
| 4,412,833 A | 11/1983 | Wiegner et al. | 604/14 |
| 4,494,278 A | 1/1985 | Kroyer et al. | 19/304 |
| 4,522,967 A | 6/1985 | Sheldon et al. | 524/377 |
| 4,600,404 A | 7/1986 | Sheldon et al. | 604/387 |
| 4,640,810 A | 2/1987 | Laursen et al. | 264/518 |
| 4,792,326 A | 12/1988 | Tews | 604/11 |
| 4,795,668 A | 1/1989 | Krueger et al. | 425/174 |
| 4,818,464 A | 4/1989 | Lau | 264/510 |
| 4,910,292 A | 3/1990 | Blount | 528/272 |
| 4,920,171 A | 4/1990 | Hutton, Jr. et al. | 524/446 |
| 4,930,942 A | 6/1990 | Keyes et al. | 406/49 |
| 4,959,208 A | 9/1990 | Chakrabarti et al. | 424/78 |
| 4,964,857 A | 10/1990 | Osborn | 604/395 |
| 4,973,656 A | 11/1990 | Blount | 528/272 |
| 5,035,886 A | 7/1991 | Chakrabarti et al. | 424/78 |
| 5,057,368 A | 10/1991 | Largman et al. | 428/397 |
| 5,063,272 A | 11/1991 | Sasse | 524/377 |
| 5,069,970 A | 12/1991 | Largman et al. | 428/373 |
| 5,089,535 A | 2/1992 | Malwitz et al. | 521/141 |
| 5,108,820 A | 4/1992 | Kaneko et al. | 428/198 |
| 5,108,827 A | 4/1992 | Gessner | 428/219 |
| 5,277,976 A | 1/1994 | Hogle et al. | 428/397 |
| 5,294,482 A | 3/1994 | Gessner | 428/287 |
| 5,300,358 A | 4/1994 | Evers | 428/286 |
| 5,312,883 A | 5/1994 | Komatsu et al. | 526/318.44 |
| 5,317,063 A | 5/1994 | Komatsu et al. | 525/330.2 |
| 5,336,552 A | 8/1994 | Strack et al. | 428/224 |
| 5,382,400 A | 1/1995 | Pike et al. | 264/168 |
| 5,405,342 A | 4/1995 | Roessler et al. | 604/364 |
| 5,466,410 A | 11/1995 | Hills | 264/172.11 |
| 5,509,913 A | 4/1996 | Yeo | 604/364 |
| 5,527,171 A | 6/1996 | Soerensen | 425/83.1 |
| 5,681,299 A | 10/1997 | Brown | 604/364 |
| 5,722,966 A | 3/1998 | Christon et al. | 604/364 |
| 5,770,528 A | 6/1998 | Mumick et al. | 442/59 |
| B15,264,268 A | 12/1998 | Luceri et al. | 428/138 |
| 5,948,710 A | * 9/1999 | Pomplun et al. | 442/341 |
| 5,981,012 A | * 11/1999 | Pomplun et al. | 428/41.8 |
| 6,117,438 A | * 9/2000 | Topolkaraev et al. | 424/404 |

* cited by examiner

WATER DISPERSIBLE PANTILINER

FIELD OF THE INVENTION

The present invention relates to a personal care product. More particularly, the present invention relates to a water dispersible pantiliner or similar product for personal use.

BACKGROUND OF THE INVENTION

Discretion, ease and convenience of disposability are important features of single use personal care products like feminine hygiene products. Likewise the goals of minimization of odor and reduction in solid waste, (since such products are typically disposed of in a landfill) are advanced by making products which are flushable. The ability to flush personal care products in a toilet also helps deliver any bodily waste products contained in the product to the waste treatment facility for proper treatment.

In order to meet these consumer desires, a number of attempts have been made to provide a product which will disperse in the water in a toilet. U.S. Pat. No. 3,550,592, for example, attempts to provide a flushable sanitary napkin by making the structure of calcium alginate and adding sodium carbonate, or some other weak base, to the toilet water. The base would be provided with the napkin at time of purchase and added to the toilet water by the user at time or disposal.

U.S. Pat. No. 5,681,299 describes a product in which the backing dissolves sufficiently to become detached from the rest of the product, when placed in a large amount of water (e.g.: a toilet). The absorbent core then becomes a slurry which will pass through sewage piping. The liner does not dissolve but is small enough to pass through the piping.

U.S. Pat. No. 5,722,966 describes a product having a fibrous top and bottom sheet and an absorbent core which are dispersible in water. The various materials used in the product are not triggerably dispersible.

Other attempts at providing flushable personal care products have focused on single use disposable diapers.

Current commercially available pantiliners may be flushed in a toilet, and, because they are quite small, will pass through the toilet fixture into the waste system piping. These pantiliners do not disperse, however, so they remain intact and retain the potential to clog the disposal system at any inopportune, and probably most inaccessible, point.

There remains a need for a personal care product in which all of the components are amenable to disposal by flushing in a toilet and which disperse relatively completely upon flushing or which are small enough to pass through the waste piping system without incident. Such a process should occur fairly quickly, without the requirement of agitation by the user or the addition of chemicals by the user. It is an object of this invention to provide a flushable pantiliner and similar items which will disperse to a great extent in the water of a toilet.

SUMMARY OF THE INVENTION

The present invention is directed to a water dispersible pantiliner which can successfully be transported through a municipal sewerage system, passing through the toilet, system piping and pumps without incident (e.g. without clogging). It can be treated at a sewerage treatment facility without causing negative effects upon the chemical, biological or other methods of waste treatment used.

The objects of the invention are met by a water dispersible pantiliner which has a triggerably dispersible body side facing liner, a garment side facing baffle, and, optionally, a triggerably dispersible absorbent core disposed between the liner and baffle. The garment baffle may be biodegradable.

In one embodiment, the invention has a peel strip overlaying a garment attachment adhesive layer which adhesively attaches the peel strip to the clothing of a wearer on one side and to one side of a baffle on the other. The baffle is in turn attached on a second side to a body facing side with a construction adhesive. The body facing side may be made from multiple layers such as a body side liner and absorbent layer.

All components of the pantiliner are substantially dispersible in water or, after detaching from the item are so small, that the pantiliner may be disposed of after use by flushing in a toilet.

BRIEF DESCRIPTION OF THE DRAWINGS

The FIGURE is a schematic side elevation showing a peel strip 1 which adhesively attaches by means of a garment attachment adhesive 2 to a barrier film or baffle layer 3 on one side. The other side of the baffle 3 attaches to an absorbent layer 5 with construction adhesive 4. The absorbent layer 5 attaches to the body side liner 6.

DEFINITIONS

Figure 1:
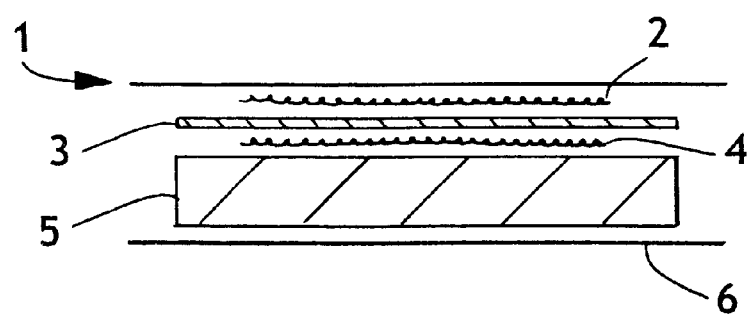

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 5 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. Nos. 5,108,827 and 5,294,482 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive. Examples of airlaying technology can be found in U.S. Pat. Nos. 4,494,278, 5,527,171, 3,375,448 and 4,640,810.

As used herein, through-air bonding or "TAB" means a process of bonding a nonwoven bicomponent fiber web in which air which is sufficiently hot to melt one of the polymers of which the fibers of the web are made is forced through the web. The air velocity is between 100 and 500 feet per minute and the dwell time may be as long as 6 seconds. The melting and resolidification of the polymer provides the bonding. Through air bonding has relatively restricted variability and since through-air bonding (TAB) requires the melting of at least one component to accomplish bonding, it is restricted to webs with two components like conjugate fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

As used herein, the term "water dispersible" refers to structure which when placed in an aqueous environment will, with sufficient time, break apart into smaller pieces. As a result, the structure once dispersed may be more advantageously processable in recycling processes or flushable in, for example, septic and municipal sewage treatment systems. If desired, such structures may be made more water dispersible or the dispersion may be hastened by the use of agitation and/or certain triggering means as are further described below. The actual amount of time will depend at least in part upon the particular end-use design criteria.

As used herein, the term "flushable" means that an item may be successfully transported through a toilet and through the typical municipal sewerage system piping and pumps without incident (i.e.: clogging).

As used herein, the term "biodegradable" means that a material degrades from the action of naturally occurring microorganisms such as bacteria, fungi and algae.

As used herein, the term "personal care product" means bandages and wound care items, diapers, training pants, swimwear, absorbent underpants, adult incontinence products, and feminine hygiene products.

As used herein, the term "pantiliner" means an absorbent feminine hygeine product which is placed in a wearer's panty to absorb bodily fluids. In addition to this commonly understood meaning, the term "pantiliner" is meant to encompass similar products like bandages and wound care items and adult (particularly male) incontinence items. These items are similar in size and function to a pantiliner and therefore are intended to be within the scope of this invention. The term pantiliner shall be used throughout this document as a sort of abbreviation for the wider class of similar products, some of which are mentioned above.

DETAILED DESCRIPTION OF THE INVENTION

The present invention is directed to a composite structure, which has a number of different components which are flushable and/or water dispersible. The required components are a body side liner or cover which is adjacent a wearer's body and which initially accepts fluids, a garment side liner or baffle which protects the wearer's clothing from staining. Optionally, an absorbent core which accepts and holds fluids from the body side liner and which is disposed between the cover and baffle may be used. Additional components like adhesives or peel strips may be added for particular product configurations or methods of construction.

The body side facing liner or cover must permit fluids to pass through it and, for flushabilty, must disperse well from the rest of the components and preferably not float. Since the body side facing liner must allow fluids to pass through it and not disintegrate during use, it must be made from a triggerable polymer. The form of the triggerable polymer is most preferably a fiber, though may be a film or foam.

In order to be effective for use in flushable personal care products, the triggerable liner must be functional in use, i.e. maintain integrity in the presence of body fluids, yet dissolve or disperse rapidly in water found in toilets. The main component of the triggerable liner of the present invention is an ion-trigger polymer. An ion-trigger polymer is one whose strength and dispersibility in water is changed depending on a very slight difference in the concentrations of a salt. More specifically, an ion-trigger polymer loses strength and disperses in tap water, but maintains strength and is insoluble in an aqueous solution which contains not less than 0.5% by weight of a neutral inorganic salt comprising a monovalent ion such as NaCl, KCl and NaBr.

It is well known that addition of an inorganic salt to an aqueous solution of a water-soluble polymer may force polymer precipitation through a salting-out phenomenon. For example, anionic polymers such as sodium salts of polyacrylate and carboxymethyl cellulose become insoluble in an aqueous solution of common salt having a concentration of 4 to 5% or higher; non-ionic polymers such as hydroxyethyl cellulose and polyvinyl alcohol (PVA) are insoluble in an aqueous solution only when the concentration of the salt is increased to about 10% or higher. This salting out of a water soluble polymer describes the change from a homogeneous polymer solution to a polymer precipitate. While an ion-trigger polymer is certainly salt-sensitive, like the simple water-soluble polymers mentioned above, there are several significant differences in the behavior of an ion-trigger polymer for flushable applications. First, the ion-trigger polymer may be sensitive to changes in ion concentration at low levels, such as 0.5% by weight of a common salt. Second, in the aqueous ionic solutions of typical body fluids, the ion trigger polymer is expected not just to be insoluble, but is required to maintain integrity and strength. Finally, the ion trigger polymer loses enough strength or integrity to disperse in tap water; but note that this dispersion does not necessarily require full dissolution, as would be typical with the simple salt-sensitive water-soluble polymers.

The feature of integrity and strength in use can be achieved by ensuring a proper "hydrophobic/hydrophilic balance" throughout the polymer chain. As used herein, the term "hydrophobic/hydrophilic balance" refers to a balance of hydrophobic and hydrophilic moieties along the polymer chain, which results in the polymer having a desired trigger property. By control of the hydrophobic/hydrophilic balance in the composition of the polymer, ion-sensitive polymers having desired in-use integrity and water-dispersibility are produced. In contrast, for simple salt-sensitive, water-soluble homopolymers, like polyvinyl alcohol, the hydrophobic/hydrophilic character is fixed by the structure of the monomer, and cannot be adjusted.

In one formulation of the triggerable polymer, the ion-trigger character is provided by a sulfonated polyester condensation polymer. The hydrophobic/hydrophilic balance can be controlled by choice of the monomers involved in the condensation reaction. The preparation of such polyesters is generally described, for example, in U.S. Pat. Nos. 4,910,292 or 4,973,656.

In addition to the sulfonated copolyesters, a variety of other trigger polymers are known in the art. U.S. Pat. No. 5,770,528 reveals methylated hydroxproplyl cellulose as an polymer with trigger controlled by temperature and ion concentration. Hydroxypropyl cellulose itself has some ion-sensitivity, but is more of a temperature-trigger material.

Indeed, U.S. Pat. No. 5,509,913 lists a variety of polymers, including poly vinyl methyl ether, polyvinyl alcohol and various cellulose polymers with temperature triggers modulated by ion concentration. These temperature-trigger polymers could have limited utility in a triggerable fiber.

Water-soluble, ion-trigger polymers are also known. For example, U.S. Pat. Nos. 5,317,063 and 5,312,883 reveal acrylic acid or methacrylic acid copolymers that are ion-sensitive. Unfortunately, these materials are not melt processable, and so not amenable to fiber production. Coating an aqueous solution of ion-trigger polymers on a water-insensitive polymer core is also possible.

It is suitable that the body facing liner be made from conjugate fibers in a sheath/core configuration so that the core gives the fibers strength and the sheath bondability. Such fibers may be crimped or crimpable according to U.S. Pat. No. 5,382,400 to Pike et al. One type of fiber to be used as the conjugate fiber has a polypropylene core and an outer sheath consisting of HB Fuller's NP2068 or NP 2074, Atochem's PEBAX MX 1074, Nippon Gohsei's Ecomaty AX10000, National Starch's 8824-71-1, 70-4395, 70-4442 copolyesters and the blends of the polymers mentioned above with some other biodegradable polymers such as aliphatic polyesters. The suitable aliphatic polyesters include, but are not limited to, polybutylene succinate, polybutylene succinate adipate, polyhydroxylbutyrate-covalerate, polycaprolactone, and polylactide and its copolymers, and the 80/20 blend of triggerable conjugate staple binder fibers mentioned above. The conjugate fibers can be blended with other less expensive fibers in a number of known process in order to reduce cost. The conjugate fiber may be blended with less expensive fibers like polyolefins, polyester, rayon, etc., in amount of from about 10/90 to 90/10, or more particularly about 50/50, by any suitable process. Examples of suitable processes include airlaying, coforming, and bonding and carding, after which the fibers may be bound together by, for example, through air bonding at an appropriate temperature. Liquid binders may also be used, such as Kymene® 557LX binder available from Hercules Inc. of Wilmington, Del. The less expensive fibers may be staple fibers which are typically 6 to 12 mm in length and about 1.5 denier so that they will not form long strands upon dispersion which could become caught on projections in the waste system piping or other parts of the treatment facility, and cause clogs. The finished body side liner 6 should be in the range of from about 10 to 500 gsm in basis weight or more particularly between about 20 and 30 gsm.

Multicomponent ionically triggerable fibers are provided in U.S. Pat. No. 5,916,678. This provides a polymer fiber in which one component comprises a water dispersible polymer that remains stable in the presence of an aqueous solution having greater than about 1000 ppm of a kosmotrope and disperses in a period not exceeding 30 minutes in an aqueous solution having less than about 1000 ppm of a kosmotrope. In one example in this application, film samples formed from National Starch 70-4442 polymer were tested for dispersion in deionized water as compared to commercially available bath tissue, substantially in accordance with "A Simple Test for Dispersion of Wet Chop Fiberglass in Water", published in the 1996 TAPPI Proceedings Nonwovens Conference and incorporated herein by reference. Five 1.5 inch (38.1 mm) long by 1.5 inch (38.1 mm) wide film samples (Sample 1) having an average weight of 0.2525 gram were placed in 1,500 ml of deionized water having a resistance greater than or equal to 18 megaohms contained in a 2,000 ml Kimax beaker, No. 14005. A Fisher Scientific Stirrer (Magnetic), Catalog No.11 -498-78H, was set at a speed setting of 7 to agitate the contents of the beaker. Using a standard timer, the period of time was measured from the point the stirrer was activated until the onset of dispersion occurred, which was defined as the point at which the first piece of sample film material broke off or away from the remaining portion of the film sample, and until full dispersion occurred, which was defined as the point at which the sample film material had dispersed into pieces having diameters not exceeding about 0.25 inch (6.35 mm).

Five single sheets of Kleenex® Premium Bath Tissue (Sample 2) available from Kimberly-Clark Corp. of Dallas, Tex., each measuring 4.0 inches (10.2 cm) by 4.5 inches (11.4 cm) and having an average weight of 0.3274 gram, were subjected to the same test procedure and the periods for the onset of dispersion and full dispersion were measured.

Finally, this test procedure was repeated by placing a single 1.5 inch (38.1 mm) by 1.5 inch (38.1 mm) sample of film (Sample 3) made from National Starch 70-4442 polymer, having a weight of 0.2029 gram, in 1,500 ml of Blood Bank Saline, 0.85% NaCl, Catalog No. B3158-1 with 0.1% sulfate anion added. The periods for onset of dispersion and full dispersion were measured. As can be seen from Table 1 below, no dispersion occurred for a period of 15 minutes, at which time the test was terminated.

TABLE 1

| Sample No. | No. of Measurements | Onset of Dispersion (seconds) | Full Dispersion (seconds) |
| --- | --- | --- | --- |
| 1 | 5 | 57.2 | 82.4 |
| 2 | 5 | 45.4 | 122.0 |
| 3 | 1 | None after 15 minutes | None after 15 minutes |

The results of the test procedures performed under this Example further illustrate that fibers employing the triggered, water-dispersible 70-4442 polymer, in accordance with the present invention, will disperse in the presence of a particular trigger component, such as the sulfate anion, at a concentration level found in excess water, while remaining substantially unaffected when exposed to the same trigger component at a concentration level typically found in body fluids, such as infant or adult urine. Moreover, the rate of dispersion compares favorably to that of commercial bath tissue products, which generally are disposed of in normal tap water, such as is found in toilet bowls.

The absorbent layer, if used, must be capable of absorbing small loadings of menses or other vaginal discharges, and urine. These amounts are generally between 0.25 and 4 grams. The absorbent layer must be triggerably dispersible since it, like the body facing side liner, must be exposed to bodily fluids while in use and not disintegrate. Particularly suitable materials are made by the coform, bonding and carding, or airlaying processes and include pulp together with water dispersible polymer binder fibers in a range from about 5/95 to 95/5 weight percent, more particularly about 70/30 weight percent and having a basis weight of from 20 to 600 gsm, more particularly about 190 gsm. Suitable polymers for the coform process include Ecomaty AX10000 from Nippon Gohsei, NP2069 and NP2074 from HB Fuller Company, 1200 Wolters Blvd, Vadnais Heights, Minn. 55110, PEBAX MX1074 from Atochem Inc., 266 Harristown Rd., PO Box 607 Glen Rock N.J. 07452 and National Starch's 70-4395, a kosmotrope. A desirable binder fiber for an airlaid process is based on a triggered resin; a polymer which is stable in the temperatures, PH and ionic concentrations that are found in body fluids such as urine, menses and blood, but is still soluble in water at the conditions typically found in a toilet bowl, i.e., lower temperatures, moderate pH and lower ionic concentrations. A preferred binder fiber is a 50/50 sheath core conjugate fiber with a core of polyolefin, typically polypropylene or polyethylene, and a sheath of a triggerable polymer, which may be a blend. Satisfactory triggerable sheath polymers are blends of copolyesters containing one or more ion sensitive functional groups, such as sulfonate and carboxylate groups and a biodegradable polymer such as an aliphatic polyester. The suitable aliphatic polyesters include, but are not limited to, polybutylene succinate, polybutylene succinate adipate, polyhydroxylbutyrate-co-valerate, polycaprolactone, and polylactide and its copolymers. One of the particular polymers which may be used is an 80/20 blend by weight of resin 70-4442 from National starch, with a poly(lactide) copolymer called HeplonE from the Chronopol Corporation of Golden, CO. Another example is an 80/20 blend by weight of resin 70-4442 with a polylactide copolymer called CPX5-2 from the Chronopol Corp. Fibers with a denier of about 3 to 6 and a length of less than 6 mm are preferred.

Suitable pulps for the absorbent include Coosa River (CR) 1654 pulp which is a southern softwood pulp, CR-2054 pulp, and high bulk additive formaldehyde free (HBAFF)

pulp which is available from the Weyerhaeuser Corporation of Tacoma, WA under the designation NHB-416 and which is a crosslinked southern softwood pulp fiber with enhanced wet modulus. NHB-416 has a chemical treatment which sets in a curl and twist, in addition to imparting added dry and wet stiffness and resilience to the fiber. Another suitable pulp is Weyerhauser's NB-41 6 southern softwood pulp.

As further illustrations of the trigger behavior integral to the present invention, tensile tests were performed on airlaid and coform nonwoven layers made with trigger binder fibers. The first example is an airlaid structure made solely with binder fiber. In this case the binder fiber was a 50/50 sheath-core of National Starch 70-4442 sheath around a polypropylene core. These fibers were prepared by Chisso Corporation of Japan, with about a 4 denier size and a 6 mm length. The fibers were then formed into an airlaid structure of about 33 gsm. The tensile strength of the nonwoven web was then tested dry, after a five minute soak in distilled water, or after a 30 minute soak in 1 weight percent of a sodium sulfate solution. A 2.5 cm by 10.2 cm (one-inch by four-inch) sample of the airlaid web was clamped by the short sides in a Vintrodyne V-1000 mini-tensile tester from Chattilone Corporation of Greensboro, N.C., and the peak load measured. For the wet tests, the web, clamps and all, was submerged in a beaker of fluid. Results are reported in Table 2 below in the row labeled "Airlaid".

As a second example of characteristic trigger behavior, a 65/35 pulp/polymer coform was made at about 150 gsm. The bonding polymer was an 80/20 blend of NS 70-4442 and HeplonE mentioned above for the sheath of a trigger binder fiber. The polymer blend was not optimized for the coform process, so formation was poor, but trigger behavior is still evident, as seen in the row labeled "Coform" in Table 2.

As a final example, a sample of airlaid cover and airlaid absorbent thermally embossed together was prepared. The binder was again a trigger 50/50 sheath-core fiber prepared by Chisso, with the polypropylene core surrounded by an 80/20 blend of NS 70-4442 and HeplonE. The 30 gsm cover was a 50/50 blend of the binder fiber and a Nyon fiber (2.2 dtex polyamide from Novalis), while the 120 gsm absorbent was a 70/30 blend of pulp (Weyerhauser NB-416) and the binder fiber. In this case the peak tensile strength was measured on an Intelect-II machine on a 2.5 cm by 15.2 cm (one-inch by six-inch) sample, with the samples for the wet tests soaked in a pan of solution and then removed from the pan for testing. Data from these measurements is reported in the row labeled "Cover/Absorbent laminates" in Table 2.

TABLE 2

| Nonwoven | Dry Strength g/in | Salt Strength g/in | Salt soak time | Water Strength g/in | Water soak time |
|---|---|---|---|---|---|
| Airlaid | 1298 | 306 | 30 minutes | 131 | 5 minutes |
| Coform | 539 | 66 | 30 seconds | 45 | 30 seconds |
| Cover/ Absorbent Laminate | 295 | 68 | 30 second | 27 | 30 seconds |

In contrast to the results in Table 2, the spunbond polypropylene cover and the coform absorbent with a polypropylene bonding polymer of the commercially available Kotex® Lightdays® pantiliner from the Kimberly-Clark Corporation, have no trigger behavior, are insensitive to both salt solution and water, and keep essentially the same level of strength dry or wet.

The barrier layer or baffle has been a particular problem for flushability. Currently used polyethylene films are not ideal for a flushable product since, while they will disperse or detach from the product, the film itself does not disperse and they tend to float in water. Polyethylene film can pass entirely through modern treatment facilities intact and be in recognizable form in the treatment plant effluent. Also suitable for use as baffles are nonwoven fabrics and foams.

Since it does not absorb bodily fluids or allow them to pass through, the baffle layer need not be triggerably dispersible. The baffle does contact bodily fluids to a degree, however, so if it is not triggerably dispersible it must be protected, by for example, an impermeable coating. The preferred structure is a water soluble or dispersible film with a barrier coating or layer to protect it from contact with bodily fluids.

One such dispersible polymer for the baffle layer of the instant invention is a blend of polyethylene oxide (PEO) and ethylene-co-acrylic acid (EAA) in a weight ratio of from about 95/5 to about 20/80, particularly about 80/20. This polymer blend has a density greater than that of water and so will sink, and is also dispersible in water. One source of a suitable polymer blend is Planet Technologies Inc., 9985 Business Park Ave., Suite A, San Diego, Calif. 92131 as product number PT-P8-200RR9. This particular product number also includes a fragrance capable of surviving melt extrusion. This blend may be extruded into a film using either the cast chill roll or blown bubble processes, which are known in the art, at a thickness range of from 10 to 100 microns. A more particularly suitable thickness is from about 20 to 30 microns. Yet another suitable dispersible but not triggerable polymer is a polyvinyl alcohol such as Ecomaty AX2000 or AX300G supplied by Nippon Gohsei, Higashi Umeda Bldg. 9-6, Nozai-cho, Kita-ku, Osaka 530, Japan.

The baffle layer polymer blend may be co-extruded with another water impervious film layer in the range of about 2 to 4 microns thick. A suitable polymer is EAA like those available from the Dow Chemical Company of Midland Mich. as Primacor 1430. Another suitable polymer is polycaprolactone like that available from Union Carbide of Danbury, Conn. as Tone P787. The water impervious layer may also be a trigger polymer such as National Starch's 70-4395 and 8824-71-1. As an alternative to co-extrusion, a water impervious layer on the water soluble portion can be added by a coating process. For example, the PEO film PTP8200RR9 from Planet Technologies Inc. can be slot coated with a 90/10 blend by weight of RT2730 poly alpha olefin from Rexene Products, Dallas, Tex. and Vybar 253 polymer from Petrolite Polymers, Tulsa Okla.

If the baffle layer is not dispersible, triggerably or otherwise, it should at least be biodegradable. If the baffle is biodegradable it can be processed through a waste water facility and will eventually disintegrate. Cellulose based material such as cellulose acetate and aliphatic polyesters such as polybutylene succinate, polybutylene succinate adipate, polyhydroxybutyrate-co-valerate, polycaprolactone, and polylactide and its copolymers are suitable cantidates. One example of a suitable material is rayon.

A number of means are available to assemble the layers of this invention. Adhesive bonding is quite satisfactory, as is thermal bonding and embossing. The pantiliner of this invention may be embossed or bonded using heat and/or pressure. The embossing may be accomplished using, for example, ultrasonic bonding and/or mechanical bonding as through the use of smooth and/or patterned bonding rolls which may or may not be heated. In addition, production means in which the layers are produced directly onto the preceding layer may be used. Such a production technique, like airlaying, results in the mechanical mixing of fibers in the boundary area of each layer and so holds it together. In short, any means known in the art successfully increase the integrity of the layers such as to produce a unified product which will remain intact through consumer use is acceptable.

Its also desired to provide some means to hold the item in place in the panty while in use. Pantiliners have traditionally accomplished this through the use of peel strips which are removed and discarded to reveal a garment adhesive. The product is then applied to the panty with the side having the garment adhesive first.

This goal can also be reached through the use of (body) heat activated adhesives which remain non-tacky at ambient temperatures but which become adhesive after equilibrating to body temperature. Its possible some small amounts of construction adhesive may be necessary to hold the pantiliner in place until the body heat activated adhesive begins to work. Other mechanical attachment means, such as a patch of microhook material which engages the fabric of the undergarment, might also provide an attachment that does not require a peel strip.

In a preferred embodiment of the instant invention, as shown in cross section in the FIGURE, invention has a peel strip 1 overlaying a garment attachment adhesive 2 which holds the pantiliner in place on the wearer's panty. The garment adhesive 2 is attached to a barrier film layer or baffle 3 which prohibits transfer of liquids from the pantiliner to the panty. The baffle 3 is adhered to the body facing side which includes an absorbent layer 5 and a body facing liner 6 with a layer of construction adhesive 4. The construction adhesive 4 attaches to an absorbent layer 5 to which is attached a body facing liner 6. Further description of each layer follows below.

The flushable peel strip 1 may be made from a paper base sheet with a water soluble binder (e.g. polyvinyl alcohol) and a silicone release coating. Such a material is available from Sansei E&M Co., Ltd, No. 18-12, 3-Chome, Roppongi, Minato-ku, Tokyo 106, Japan and from International Paper, Akrosil Division, 206 Garfield Ave., PO Box 8001, Menasha Wis. 54952-8001. A flushable release strip may also be constructed by putting a thin layer of release coating on a water soluble film.

The garment attachment adhesive 2 should be one which will minimize adhesion and detackify once placed in water. Suitable adhesives may be supplied by National Starch and Chemical Corporation, Finderne Ave., Bridgewater, N.J. 08807 as product number 7699-67-2, or by Findley Adhesive Inc., 11320 Watertown Plank Rd., Wauwatosa, Wis. 53226-3413 as product number H2427(N2). The garment adhesive 2 must be applied in an effective amount by any effective means. One method is by spraying the adhesive 2 onto the baffle 3 in an amount of about 20 gsm in a strip about 25 mm wide. The effective amount of adhesive 2 may, of course, vary, based on the type of adhesive used, stiffness of the product, performance requirements, and total area of application. Its believed, however, that the effective amount will vary between about 10 and 60 gsm.

The construction adhesive 4 should be one which will release in water to minimize wet rigidity and so enhance the flushability of the product. Suitable polymers include National Starch's product numbers7699-94-1, 7187-119-2, 8328-122-1 and Findley Adhesives' number H-9186. As with the garment adhesive 2, an effective amount of adhesive must be used. This may be an amount between about 1 and 50 gsm. The adhesive may be applied by any method know in the art.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A water dispersible pantiliner consisting essentially of:
   a peel strip comprising a paper base sheet coated with a polyvinyl alcohol binder and silicone release agent, and;
   a water soluble garment attachment adhesive which adhesively attaches said peel strip to a first side of a baffle, said garment attachment adhesive present in an amount between 10 and 60 gsm, and;
   said baffle comprising a blend of polyethylene oxide and ethylene co-acrylic acid in an amount of about between about 20/80 and 95/5 weight percent, and;
   a construction adhesive which adhesively attaches said baffle to an absorbent core which is in turn attached to a body side liner, said construction adhesive present in an effective amount, and;
   said absorbent core comprising pulp and water dispersible polymer fibers in a range of about 5/95 to 95/5 weight percent, and;
   said body side liner comprising crimped water dispersible sheath core conjugate fibers.

* * * * *